United States Patent [19]

Marciel

[11] Patent Number: Plant 7,560

[45] Date of Patent: Jun. 18, 1991

[54] MINIATURE ROSE NAMED DEVCLAVEL

[75] Inventor: Stanley G. Marciel, Aptos, Calif.

[73] Assignee: DeVor Nurseries, Inc., Watsonville, Calif.

[21] Appl. No.: 507,561

[22] Filed: Apr. 11, 1990

[51] Int. Cl.[5] ..... A01H 5/00

[52] U.S. Cl. ..... Plt./10

[58] Field of Search ..... Plt./7, 9, 10

*Primary Examiner*—Howard J. Locker

*Attorney, Agent, or Firm*—Charles W. Rummler

[57] ABSTRACT

A new and distinct miniature rose plant specially adapted for pot plant culture and particularly distinguished by its continuous and profusely blooming habit extending from early Spring through mid-season to late Fall on a small compact bush which reaches a height of about 20 cm. in the course of twelve weeks of growth in a 4 in. pot. This plant is free branching and blooms the year around under greenhouse conditions. This plant has abundant foliage and a vigorous, strong and upright growth habit.

1 Drawing Sheet

BACKGROUND OF THE NEW PLANT

This miniature rose plant originated as a seedling of a hybrid produced by me at my nursery at Watsonville, Calif., as a result of my crossing the variety 'Scarlet Sunblaze' with pollen of a unnamed seedling selected from rose plants maintained at my nursery for breeding purposes. The present seedling was selected for propagation because of its profuse production of relatively large blooms on a plant of ideal size for pot plant culture. Propagation of this selected seedling was done by me at Watsonville by means of cuttings and successive generations of this plant, all retaining the distinctive characteristics of the original seedling have demonstrated that the novel characteristics hold true and appeared to be firmly fixed.

DESCRIPTION OF THE DRAWING

My new miniature rose plant is illustrated by the accompanying photographic drawings which, in full color, show the novel characteristics of this plant, FIG. 1 showing the top and bottom sides of a typical leaf and a series of buds in several stages of development terminating in a face view of a mature blossom.

DESCRIPTION OF THE NEW VARIETY

Figure 1:
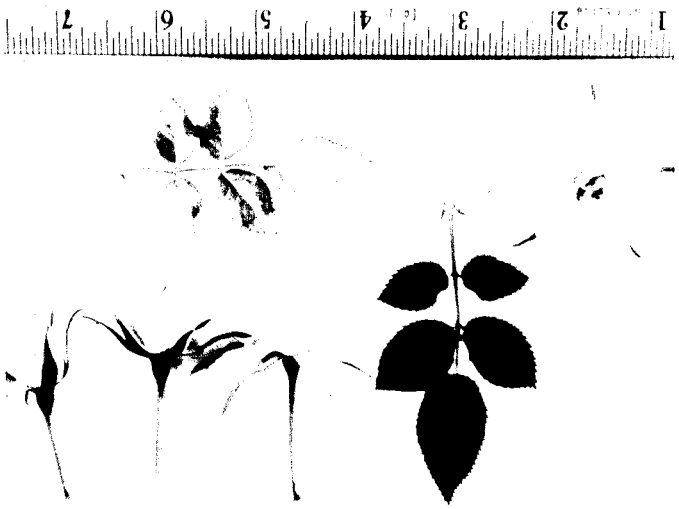
Figure 2:
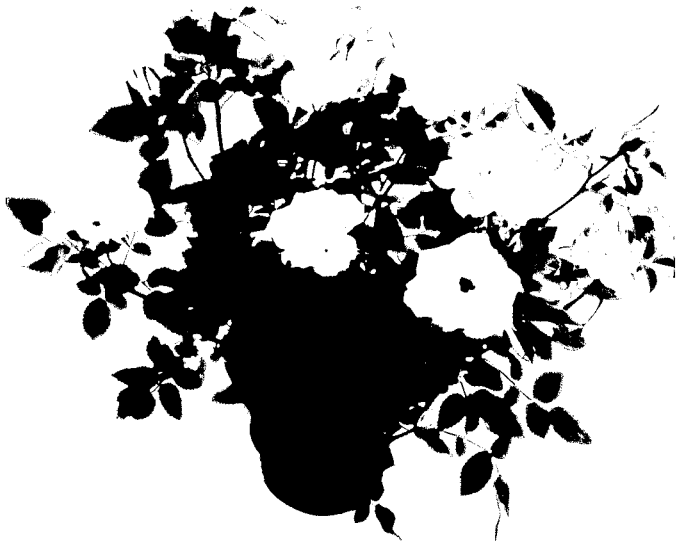
FIG. 2 is an elevational view of my miniature rose plant in full bloom and grown as a pot plant, the color rendition being as nearly true to that herein specified as is reasonably possible to obtain by conventional photographic procedures.

The following is a detailed description of my new miniature rose plant based upon observation of plants grown in greenhouse as well as out of doors at my Watsonville nursery, the color designations specified herein being according to the R.H.S. Colour Chart published by The Royal Horticultural Society of London, England.

THE PLANT

Origin: Seedling.

Parentage:

*Seed parent.*—The variety Scarlet Sunblaze (unpatented).

*Pollen parent.*—An unnamed and unpatented seedling selected and tagged from my rose plant collection at Watsonville, Calif.

Classification:

*Botanic.*—Hybrid miniature rose plant.

*Commercial.*—Miniature pot rose.

Form: Small, compact bush.

Height: About 20 cm. at twelve weeks growth in a 4 in. pot.

Growth habit: Vigorous, upright and free branching with good strength.

Flower stem:

*Length.*—About 50 to 60 mm.

Foliage:

*Quantity.*—Medium.

*Number of leaves.*—5 or 6 from last flower cut.

*Size.*—About 64 mm. long.

*Leaflets.*—Number: 3,5, or 7. Size: About 28 mm. long and 16 mm. wide in average. Shape: Oval with denticulate margin. Texture: Leathery and smooth. Aspect: Glossy. Color: Upper side — Greyed Green 147-A. Under side — Greyed Green 191-A.

*Stipules.*—Hairy adnate.

*Rachis.*—About 34 mm. for 3 part leaf; and about 53 mm. for 7 part leaf.

*Petioles.*—About 9 to 11 mm. long.

Ribs and veins: Very slightly depressed on upper side and rounded on lower side.

Thorns: None.

THE BUD

Size: Small.

*Diameter.*—About 13 mm.

*Length.*—About 15 mm.

Shape: Slender, tapering and pointed.

Rate of opening: Slow.

Color of petals:

*When sepals first divide.*—Red 53-A.

*When petals begin to unfurl.*—Red 61-B.

Sepals:

*Number.*—Five.

*Shape.*—Spreading with some leaf pointed.

*Character.*—The sepals are hooded over the bud before dividing and curl back when flowers open.

*Color.*—Inside — 191-A and covered with white hairs. Outside — Yellow Green 146-A.

Calyx:

*Shape.*—Funnel shaped.

*Size.*—Small.

*Splitting.*—Calyx does not split.

*Aspect.*—Smooth.

Flower stem:

*Length.*—About 50 to 60 mm. and hairy.

*Character.*—Erect and slender.

*Color.*—Yellow Green 144-A.

THE FLOWER

Blooming habit: Continuous and profusely from early Spring through mid-season to late Fall; blooming freely year round under glass.

Size of flower: Medium.

*Diameter.*—About 41 mm. when bloom is about ¾ open.

*Depth.*—About 9 mm.

Borne: Singly.

Form:

*When bloom first opens.*—Cup shaped.

*When bloom matures.*—Slightly flattened.

Petalage:

*Number.*—About 39.

*Arrangement.*—Imbricated.

*Form.*—Oval with slightly ruffled margin and pointed apex.

*Texture.*—Soft.

*Appearance.*—Velvety.

*Color.*—Outer petals body — Red Purple 61-B with base of 1-C. Reverse side — 63-A. Inside petals body — Red 53-A with base of Yellow 4-B. Reverse side — 59-C with base of 4-C.

Petaloids:

*Number.*—About 13.

*Length.*—About 9 mm.

*Color.*—Red 53-A.

*Base.*—Yellow 3-C.

Flower stem:

*Length.*—About 50 to 60 mm.

*Color.*—Yellow Green 144-A.

*Character.*—Sturdy and upright.

Fragrance: Mild.

Discoloration after full bloom: Slightly fading.

Disease resistance: Moderately resistant to mildew, rust, and black spots as observed at Watsonville, Calif.

Lasting quality: Long lasting on the plant and moderate as a cut flower.

THE REPRODUCTIVE ORGANS

Stamens:

*Number.*—About 69.

*Arrangement.*—Slightly introrse.

*Anthers.*—Size: About 1 to 2 mm. Color: Yellow Orange 22-A.

*Filaments.*—Length: About 3 mm. Color: Green Yellow 1-C.

*Pollen.*—Color: Yellow Orange 22-A.

Pistils:

*Number.*—About 51.

*Styles.*—Length: About 6 mm. Color: 157-A.

*Stigmas.*—Color: Yellow Orange 19-B.

Character of the ovaries: Normal.

I claim:

1. The new and distinct miniature rose variety, substantially as herein shown and described, characterized by its profuse and continuous production of relatively large flowers having a dark red coloration on a pot plant having a height of about 20 cm., a moderate quantity of foliage and a vigorous, upright, free branching growth habit.

* * * * *

R86032-91P